United States Patent
Schwab

(10) Patent No.: US 11,607,200 B2
(45) Date of Patent: Mar. 21, 2023

(54) METHODS AND SYSTEM FOR CAMERA-AIDED ULTRASOUND SCAN SETUP AND CONTROL

(71) Applicant: GE Precision Healthcare LLC, Milwaukee, WI (US)

(72) Inventor: Mario Schwab, Fornach (AT)

(73) Assignee: GE Precision Healthcare LLC, Wilwaukee, WI (US)

( * ) Notice: Subject to any disclaimer, the term of this patent is extended or adjusted under 35 U.S.C. 154(b) by 691 days.

(21) Appl. No.: 16/539,991

(22) Filed: Aug. 13, 2019

(65) Prior Publication Data
US 2021/0045717 A1    Feb. 18, 2021

(51) Int. Cl.
| A61B 8/00 | (2006.01) |
| A61B 5/1171 | (2016.01) |
| A61B 5/11 | (2006.01) |
| G06T 7/20 | (2017.01) |
| G06T 7/70 | (2017.01) |

(52) U.S. Cl.
CPC .............. *A61B 8/54* (2013.01); *A61B 5/1114* (2013.01); *A61B 5/1116* (2013.01); *A61B 5/1128* (2013.01); *A61B 5/1176* (2013.01); *A61B 8/4263* (2013.01); *A61B 8/585* (2013.01); *G06T 7/20* (2013.01); *G06T 7/70* (2017.01); *G06T 2207/30004* (2013.01)

(58) Field of Classification Search
CPC ....... A61B 5/1127; A61B 5/1128; A61B 8/54; A61B 5/1176; A61B 8/585
See application file for complete search history.

(56) References Cited

U.S. PATENT DOCUMENTS

| 6,951,543 B2 | 10/2005 | Roundhill |
| 9,008,385 B2 | 4/2015 | Baym et al. |
| 9,953,149 B2 | 4/2018 | Tussy |
| 10,893,851 B2 * | 1/2021 | Kruecker ............. A61B 8/5246 |
| 2006/0071135 A1 | 4/2006 | Trovato |
| 2007/0238981 A1 * | 10/2007 | Zhu ........................ A61B 34/20 |
| | | 600/424 |
| 2012/0239493 A1 * | 9/2012 | Zughaib ................. G06Q 10/08 |
| | | 705/14.49 |
| 2013/0150710 A1 * | 6/2013 | Zentgraf ................ A61B 5/062 |
| | | 600/424 |
| 2013/0158397 A1 * | 6/2013 | K. ........................... G16Z 99/00 |
| | | 600/437 |
| 2013/0245428 A1 * | 9/2013 | Banjanin .............. A61B 8/4263 |
| | | 600/424 |
| 2017/0312035 A1 * | 11/2017 | May ....................... A61B 5/064 |
| 2018/0103912 A1 | 4/2018 | Canfield et al. |
| 2018/0140270 A1 | 5/2018 | Profio et al. |
| 2018/0225993 A1 * | 8/2018 | Buras ................... A61B 8/4263 |
| 2019/0041302 A1 * | 2/2019 | Hunt ................. G01N 35/1011 |
| 2021/0045717 A1 * | 2/2021 | Schwab .................... G06T 7/20 |

* cited by examiner

Primary Examiner — Oommen Jacob
(74) Attorney, Agent, or Firm — McCoy Russell LLP

(57) ABSTRACT

Methods and systems are provided for adjusting settings of an ultrasound exam based on monitoring of the exam with an optical camera. One example method includes acquiring images of an ultrasound exam via a camera, analyzing the acquired images in real-time to build a spatial exam model, and adjusting settings of the ultrasound exam in real-time based on the spatial exam model.

17 Claims, 4 Drawing Sheets

METHODS AND SYSTEM FOR CAMERA-AIDED ULTRASOUND SCAN SETUP AND CONTROL

FIELD

Embodiments of the subject matter disclosed herein relate to medical imaging, and more particularly, to systems and methods for automating patient setup in ultrasound imaging.

BACKGROUND

An ultrasound exam typically includes a user (e.g., a sonographer or other clinician) applying an ultrasound probe to a patient's body. The ultrasound probe may be configured to transmit and receive ultrasound signals that are processed into an ultrasound image by a workstation or device operatively coupled the ultrasound probe. The user may perform a series of steps before the ultrasound exam to set up the workstation or device, such as entering patient information and selecting system settings. The user may perform additional steps during the ultrasound exam, such as adjusting the system settings, activating/deactivating the ultrasound probe, freezing the image, etc.

BRIEF DESCRIPTION

In one embodiment, a method comprises acquiring images of an ultrasound exam via a camera, analyzing the acquired images in real-time to build a spatial exam model, and adjusting settings of the ultrasound exam in real-time based on the spatial exam model.

Thus, settings for performing the ultrasound exam may be automatically adjusted based on the analyzed images received from the camera. As one example, the spatial exam model may include identifying and tracking a user performing the ultrasound exam via an ultrasound imaging system, the ultrasound imaging system including an ultrasound probe. As another example, the spatial exam model may include identifying and tracking the ultrasound probe. As still another example, the spatial exam model may include identifying and tracking a patient on which the ultrasound exam is being performed. By automatically adjusting the ultrasound exam settings based on the spatial exam model, a number of steps performed by the user prior to initiation of scanning during the ultrasound exam as well as during the scanning may be reduced, thereby saving time during the ultrasound exam process.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 1:
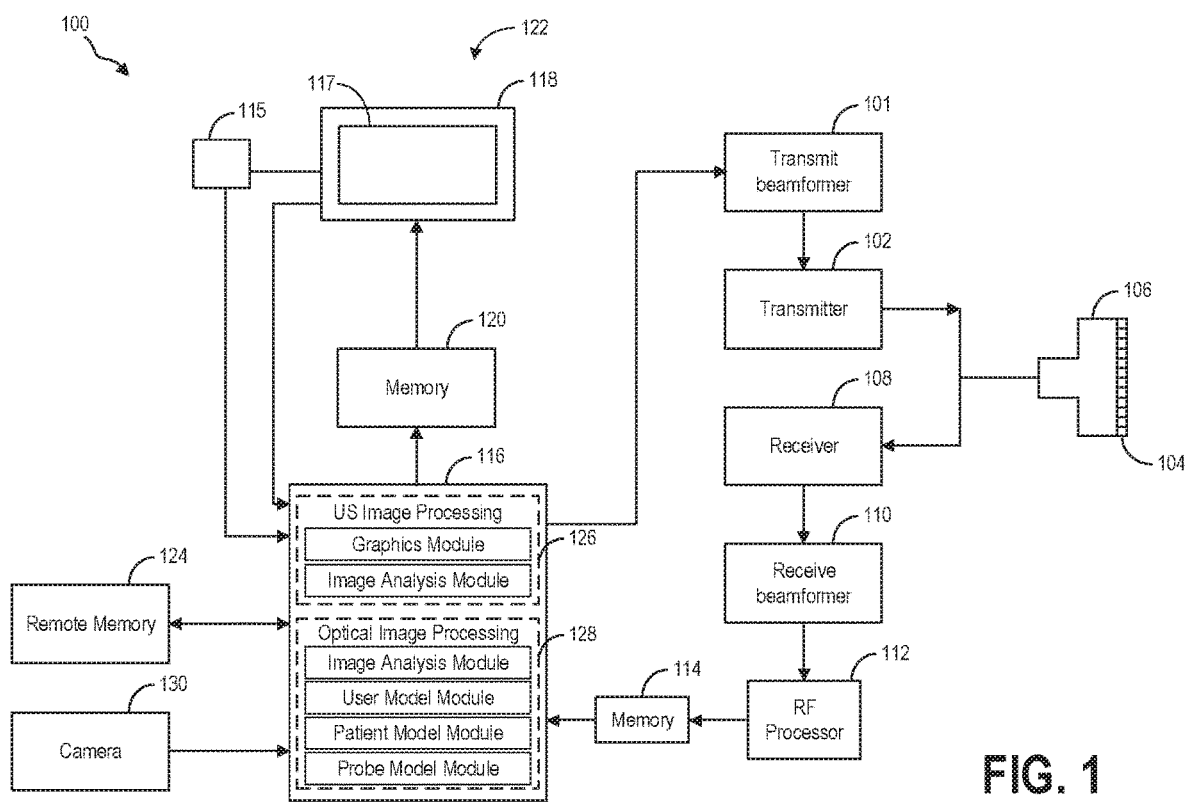
FIG. 1 schematically shows a block diagram of an example ultrasound imaging system.
Figure 2:
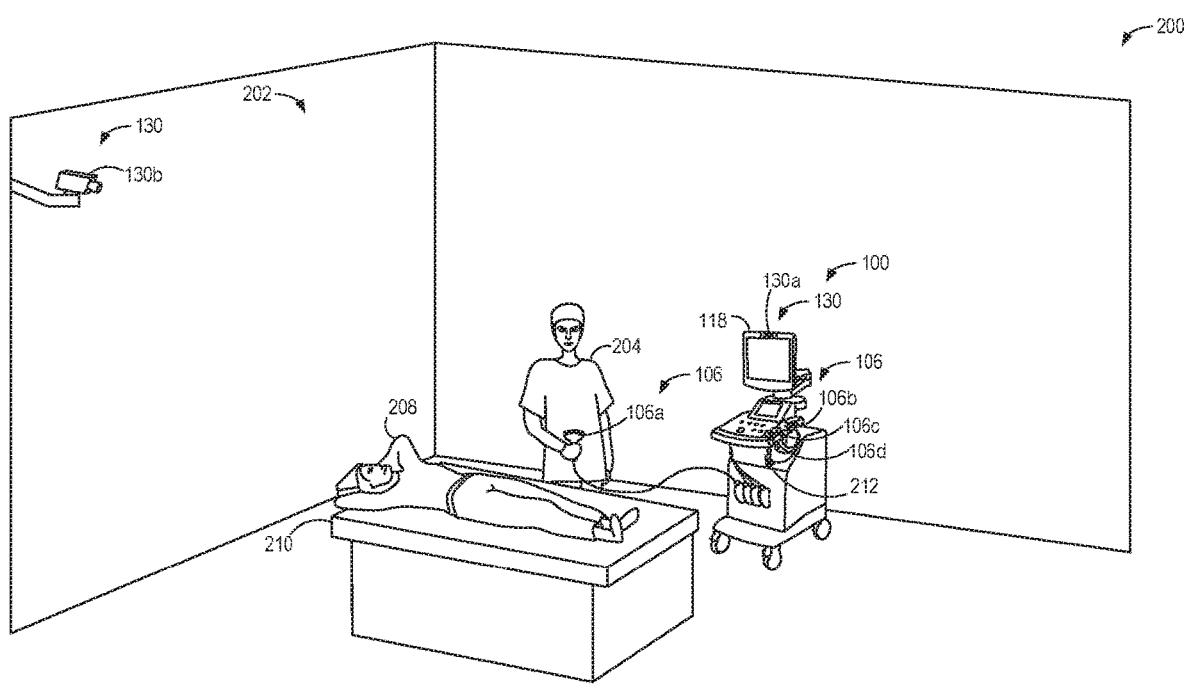
FIG. 2 illustrates an example ultrasound exam environment including an optical camera.
Figure 3:
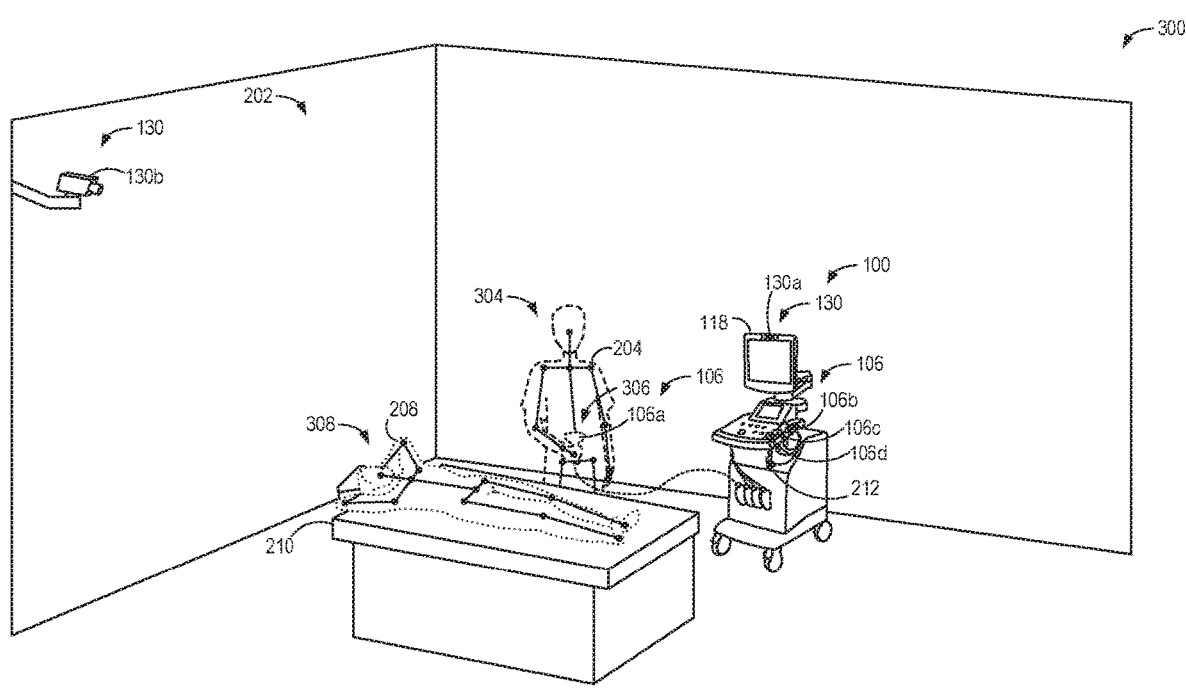
FIG. 3 illustrates building a spatial ultrasound exam model based on images captured by the camera.

The following description relates to various embodiments of an imaging system, such as the ultrasound imaging system shown in FIG. 1. In particular, methods and systems are provided for optical camera-aided ultrasound imaging system setup and exam control based on images acquired by the optical camera. The optical camera may capture images of an ultrasound exam room, including of the ultrasound imaging system, a patient, and a user of the ultrasound imaging system, such as illustrated in FIG. 2. An electronic controller of the ultrasound imaging system may analyze the images to identify patient information (e.g., patient identity, patient body mass), user (e.g., sonographer) information, and ultrasound probe position/motion, for example, and build a corresponding spatial exam model in real-time, as illustrated in FIG. 3. The spatial exam model may be used to adjust settings of the ultrasound system prior to and during patient scanning, such as according to the example method of FIG. 4. An advantage that may be realized in the practice of some embodiments of the described systems and techniques is that automating ultrasound exam setup reduces preparation and scanning time of the ultrasound exam, increasing scan throughput and/or enabling the user to focus on the patient instead of performing procedural tasks at a workstation.

Turning now to the figures, FIG. 1 illustrates a block diagram of a system 100 according to one embodiment. In the illustrated embodiment, the system 100 is an imaging system and, more specifically, an ultrasound imaging system. However, it may be understood that embodiments set forth herein may be implemented using other types of medical imaging modalities (e.g., MM, CT, PET/CT, and SPECT). As shown, the ultrasound imaging system 100 includes multiple components. The components may be coupled to one another to form a single structure, may be separate but located within a common room, or may be remotely located with respect to one another. For example, one or more of the modules described herein may operate in a data server that has a distinct and remote location with respect to other components of the ultrasound imaging system 100, such as a probe and user interface. Optionally, the ultrasound imaging system 100 may be a unitary system that is capable of being moved (e.g., portably) from room to room. For example, the ultrasound imaging system 100 may include wheels or be transported on a cart.

In the illustrated embodiment, the ultrasound imaging system 100 includes a transmit beamformer 101 and transmitter 102 that drives an array of elements 104, for example, piezoelectric crystals, within a diagnostic ultrasound probe 106 (or transducer) to emit pulsed ultrasonic signals into a body or volume (not shown) of a subject. The elements 104 and the probe 106 may have a variety of geometries. The ultrasonic signals are back-scattered from structures in the body, for example, blood vessels and surrounding tissue, to produce echoes that return to the elements 104. The echoes are received by a receiver 108. The received echoes are provided to a receive beamformer 110 that performs beamforming and outputs a radio frequency (RF) signal. The RF signal is then provided to an RF processor 112 that processes the RF signal. Alternatively, the RF processor 112 may include a complex demodulator (not shown) that demodulates the RF signal to form quadrature (IQ) data pairs representative of the echo signals. The RF or IQ signal data may then be provided directly to a memory 114 for storage (for example, temporary storage). In some examples, the beamformer may receive IQ data as a single channel input, and as such, the beamformed signal may include IQ data.

The system 100 also includes a system controller 116 that includes a plurality of modules, which may be part of a single processing unit (e.g., processor) or distributed across multiple processing units. The system controller 116 is configured to control operation of the system 100. The system controller 116 may include an ultrasound (US) image processing module 126 that receives image data (e.g., ultrasound signals in the form of RF signal data or IQ data pairs) and processes the image data. The ultrasound image processing module 126 may include one or more sub-modules, such as a graphics module and an image analysis module, as will be further described below. For example, the ultrasound image processing module 126 may process the ultrasound signals to generate slices or frames of ultrasound information (e.g., ultrasound images) for displaying to the operator. When the system 100 is an ultrasound system, the ultrasound image processing module 126 may be configured to perform one or more processing operations according to a plurality of selectable ultrasound modalities on the acquired ultrasound information. By way of example only, the ultrasound modalities may include color-flow, acoustic radiation force imaging (ARFI), B-mode, A-mode, M-mode, spectral Doppler, acoustic streaming, tissue Doppler module, C-scan, and elastography. The generated ultrasound images may be two-dimensional (2D) or three-dimensional (3D). When multiple two-dimensional (2D) images are obtained, the image-processing module may also be configured to stabilize or register the images.

Acquired ultrasound information may be processed by the ultrasound image processing module 126 in real-time during an imaging session (or scanning session) during an ultrasound exam as the echo signals are received. Additionally or alternatively, the ultrasound information may be stored temporarily in the memory 114 during an imaging session and processed in less than real-time in a live or off-line operation. An image memory 120 is included for storing processed slices of acquired ultrasound information that are not scheduled to be displayed immediately. The image memory 120 may comprise a suitable data storage medium, for example, a permanent storage medium, removable storage medium, and the like. Additionally, the image memory 120 may be a non-transitory storage medium. Image memory 120 may additionally or alternatively include temporary storage, such as a first-in-first-out buffer.

The system controller 116 may be in communication (e.g., wired or wireless communication) with a remote device that includes a remote memory 124. In one example, the remote memory 124 may be part of a picture archiving and communication system (PACS) that is configured to store patient medical histories, imaging data, test results, diagnosis information, management information, and/or scheduling information, for example. The remote memory 124 may comprise a PACS server that includes computer-readable storage media suitable for storing image data for later retrieval and viewing at a PACS workstation, for example.

The system controller 116 is also operably connected to a user interface 122 that enables an operator to control at least some of the operations of the system 100. The user interface 122 may include hardware, firmware, software, or a combination thereof that enables the operator (e.g., user) to directly or indirectly control operation of the system 100 and the various components thereof. As shown, the user interface 122 includes a display device 118 having a display area 117. In some embodiments, the user interface 122 may also include one or more user interface input devices 115, such as a physical keyboard, mouse, and/or touchpad. In one embodiment, a touchpad may be configured with the system controller 116 and display area 117 such that when a user moves a finger/glove/stylus across the face of the touchpad, a cursor atop the ultrasound image on the display area 117 moves in a corresponding manner. In an embodiment, the display device 118 is a touch-sensitive display (e.g., touchscreen) that can detect a presence of a touch from the operator on the display area 117 and can also identify a location of the touch in the display area 117. The touch may be applied by, for example, at least one of an individual's hand, glove, stylus, or the like. As such, the touch-sensitive display may also be characterized as an input device that is configured to receive inputs from the operator. The display device 118 also communicates information from the controller 116 to the operator by displaying the information to the operator. The display device 118 and/or the user interface 122 may also communicate audibly. The display device 118 is configured to present information to the operator during the imaging session. The information presented may include ultrasound images, graphical elements, user-selectable elements, and other information (e.g., administrative information, personal information of the patient, and the like).

During operation, the ultrasound imaging system 100 may acquire data, for example, volumetric data sets, by various techniques (for example, 3D scanning, real-time 3D imaging, volume scanning, 2D scanning with probes having positioning sensors, freehand scanning using a voxel correlation technique, scanning using 2D or matrix array probes, and the like). Ultrasound images of the system 100 may be generated from the acquired data (at the controller 116) and displayed to the operator or user on the display device 118. The graphics module and the image analysis module, among other potential modules of the ultrasound image processing module 126, may coordinate with one another to present information to the operator during and/or after the imaging session. For example, the graphics module may be configured to display designated graphics along with the ultrasound image on the display device 118, such as graphical outlines that represent lumens or vessel walls in the acquired image. The graphics module and/or image analysis module within the ultrasound image processing module 126 of system controller 116 may also be configured to generate a 3D rendering or image (not shown) of an imaged structure.

The screen of the display area 117 of the display device 118 is made up of a series of pixels that display the data acquired with the probe 106 and processed by the ultrasound image processing module 126. The acquired data include one or more imaging parameters calculated for each pixel or group of pixels (for example, a group of pixels assigned the same parameter value) of the display, where the one or more calculated image parameters includes one or more of an intensity, velocity, color flow velocity, texture, graininess, contractility, deformation, and rate of deformation value. The series of pixels then make up the displayed image generated from the acquired ultrasound data. As mentioned above, the data acquired with the probe 106 and processed by the controller 116 may be 2D or 3D data. For example, traditionally, B-mode images, otherwise known as 2D images, may be generated from A-mode information. In A-mode, where A stands for amplitude, information of the reflected signal in a single ultrasound beam is continually displayed as distance from the probe and intensity, which are shown by position and amplitude in a line on an oscilloscope. A-mode information from many beams typically forms a sector in a plane of the body, which is then shown as pixel intensity on a monitor in what is known as B-mode, where B stands for brightness. B-mode may be used for anatomic localization, assessment, and orientation in the body and as a background display of other information (e.g., Doppler signals), and may also include 3D imaging data.

A 3D medical imaging dataset acquired with the probe 106 includes a volume dataset including a plurality of voxels. Each voxel, or volume-element, is assigned a value or intensity. Additionally, each voxel may be assigned an opacity as well. The value or intensity may be mapped to a color according to some embodiments. As one example, a volume-rendered image may be generated from the 3D dataset using a ray casting technique. For example, the controller 116 may cast a plurality of parallel rays from a view plane of the display device 118 (which comprises the series of pixels) through the 3D medical imaging dataset. It should be appreciated that multiple rays may be cast in order to assign values to all of the pixels within the view plane. The controller 116 may use a "front-to-back" or a "back-to-front" technique for volume composition in order to assign a value to each pixel in the view plane that is intersected by the ray. For example, starting at the front—that is, the direction from which the image is viewed—the intensities of all the voxels along the corresponding ray may be summed. An opacity value, which corresponds to light attenuation, is assigned to each voxel. The intensity is multiplied by the opacity of the voxels along the ray to generate an opacity-weighted value. These opacity-weighted values are then accumulated in a front-to-back or in a back-to-front direction along each of the rays. The process of accumulating values is repeated for each of the pixels in the view plane in order to generate a volume-rendered image. In this way, each pixel used to form the image displayed on the display device 118 may have an intensity, or brightness, value associated with it.

The system controller 116 may also house an optical image processing module 128, which may process images received by the system controller 116 from a camera 130. The camera 130 may be mounted in various locations on or around the ultrasound imaging system 100. As one example, the camera 130 may be mounted on the display device 118. As another example, the camera 130 may be wall-mounted in a same room as the system 100, particularly the same room as the probe 106 when the system 100 spans multiple locations (e.g., an exam room). Further, the camera 130 may include one or more optical (e.g., visible light) cameras, one or more infrared (IR) cameras, or a combination of optical and IR cameras positioned in one or more locations (or view angles), as will be described below with respect to FIG. 2. As one example, the camera 130 may be a digital camera configured to acquire a series of images (e.g., frames) at a programmable frequency (e.g., frame rate). Further, the camera 130 may output acquired images to the system controller 116 in real-time so that they may be processed by the optical image processing module 128 in real-time. In some examples, the camera 130 may be calibrated with respect to a world coordinate system (e.g., world space x, y, z).

The optical image processing module 128 may include an image analysis module, a user model module, a patient model module, and a probe model module. The image analysis module of the optical image processing module 128 may access images/videos (e.g., an image library) stored in memory and analyze the images received from the camera 130 in real-time to identify one or more features within each of the received image. As one example, the image analysis module may compare a real-time image received from the camera 130 to one stored in memory to identify the user, the patient, and the probe 106 within the ultrasound exam environment. For example, the image analysis module may enable the system controller 116 to distinguish the user from the patient and any other human subjects in the exam room, the patient from the user and any other human subject in the exam room, and the probe 106 from other medical equipment in the exam room. The image analysis module may further use a computer vision model or algorithm stored within a memory of the system controller 116, such as a biometric algorithm, to facially recognize the user (and, in some examples, the patient) in order to positively identify the user (and the patient). For example, the image analysis module may house both an image library and separate instructions for analyzing the received images apart from the image library, and both of these approaches may be used for distinguishing the user, the patient, and the probe 106 from other objects/persons in the received images (and from each other) as well as for positively identifying the user and/or the patient, at least in some examples. Further, the image analysis module may use conventional machine learning approaches, such as convolutional neural networks, to reduce pre-processing.

Further, the system controller 116 may house instructions for building a user model via the user model module, building a patient model via the patient model module, and building a probe model via the probe model module based on the analyzed images. The system controller 116 may further build an overall spatial exam model based on the interrelation between the user model, the patient model, and the probe model and identify exam actions based on the spatial exam model, as will be further described below with respect to FIGS. 3 and 4. For example, the exam actions may include activating the probe 106 to start a scan, deactivating the probe 106 to stop scanning, and auto-freezing an ultrasound image on display device 118 when the user holds probe 106 still during the scan.

As used herein, the terms "system," "unit," or "module" may include a hardware and/or software system that operates to perform one or more functions. For example, a module, unit, or system may include a computer processor, controller, or other logic-based device that performs operations based on instructions stored on a tangible and non-transitory computer readable storage medium, such as a computer memory. Alternatively, a module, unit, or system may include a hard-wired device that performs operations based on hard-wired logic of the device. Various modules or units shown in the attached figures may represent the hardware that operates based on software or hardwired instructions, the software that directs hardware to perform the operations, or a combination thereof.

"Systems," "units," or "modules" may include or represent hardware and associated instructions (e.g., software stored on a tangible and non-transitory computer readable storage medium, such as a computer hard drive, ROM, RAM, or the like) that perform one or more operations described herein. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described above. Additionally or alternatively, one or more of these devices may be hard-wired with logic circuits to perform these operations.

Turning now to FIG. 2, an example ultrasound exam environment 200 is shown. In the particular example of FIG. 2, the ultrasound exam environment 200 is confined to an exam room 202 that includes the ultrasound imaging system 100 positioned therein. As such, components previously introduced in FIG. 1 are numbered the same and may not be introduced. Further, it should be understood that components of the system 100 described above with respect to FIG. 1 may not be specifically illustrated in FIG. 2 (such as the system controller 116), although they may be included and may be positioned within the exam room 202 (e.g., integrated in the ultrasound imaging system 100) or in location(s) remote from the exam room 202 (such as the remote memory 124 introduced in FIG. 1).

The ultrasound exam environment 200 further includes a user 204 and a patient 208, the patient 208 positioned on an exam table 210. However, in other examples, a remote exam may be performed, and the user 204 may not be present in the exam room 202. In the example illustrated in FIG. 2, the ultrasound imaging system 100 includes a plurality of probes 106 that may be stored in a probe holder 212, including probes 106a, 106b, 106c, and 106d. For example, each of the probes 106a, 106b, 106c, and 106d may be assigned to a specific position (or probe slot) within the probe holder 212, which may be programmed in the system controller 116 of the ultrasound imaging system 100. Further, the probe type of each probe 106a, 106b, 106c, and 106d may be programmed in the system controller 116. For example, probe 106a may be a curvilinear probe that is assigned to be stored in a first position of the probe holder 212, probe 106b may be a different type of curvilinear probe that is assigned to be stored in a second position of the probe holder 212, probe 106c may be a linear probe that is assigned to be stored in a third position of the probe holder 212, and probe 106d may be a phased array probe that is assigned to be stored in a fourth position of the probe holder. In the example illustrated in FIG. 2, the user 204 has selected probe 106a, which is removed from probe holder 212. In contrast, probes 106b, 106c, and 106d remain in their respective positions within the probe holder 212.

The ultrasound exam environment 200 further includes a first camera 130a mounted on the display device 118 and a second camera 130b mounted on a wall of exam room 202, the first camera 130a and the second camera 130b each included in the camera 130. The first camera 130a and the second camera 130b are positioned to acquire images having different view angles. By including the different view angles, the system controller 116 may receive a more complete image of the overall ultrasound exam environment 200 than when only one view angle is included.

Further, the first camera 130a and/or the second camera 130b may each include more than one lens and more than one image sensor. For example, the first camera 130a is shown having two lenses. The first lens may direct light to a first, visible light image sensor (e.g., a charge-coupled device or a metal-oxide-semiconductor) while the second lens may direct light to a thermal imaging sensor (e.g., a focal plane array), enabling the first camera 130a to collect light of different wavelength ranges for producing both visible and thermal images.

As mentioned above, the system controller 116 of the ultrasound imaging system 100 may receive the images from the camera 130 (e.g., the first camera 130a and the second camera 130b) as they are acquired and process the received images in real-time to build a spatial exam model. Turning now to FIG. 3, an example spatial exam model 300 is shown. Components previously introduced in FIGS. 1 and 2 are numbered the same and may not be reintroduced.

Specifically, FIG. 3 depicts how the system controller 116 may transform the ultrasound exam environment 200 shown in FIG. 2 into the spatial exam model 300. The spatial exam model 300 includes a user model 304, a probe model 306, and a patient model 308. As an example, the system controller 116 may use the image information received from camera 130 in combination with instructions stored in the optical image processing module 128 shown in FIG. 1 to identify the user 204, the selected probe 106a, and the patient 208 and build the user model 304, the probe model 306, and the patient model 308, respectively. In one example, the user model 304 and the patient model 308 may each include skeletal tracking. The skeletal tracking may identify various skeletal joints of a human subject (e.g., the user 204 or the patient 208), which may correspond to actual joints of the human subject, centroids of various anatomical structures, terminal ends of the human subject's extremities, and/or points without a direct anatomical link to the human subject, and map a virtual skeleton onto the human subject. As each joint of the human subject has at least three degrees of freedom (e.g., world space x, y, z), each joint of the virtual skeleton used for the skeletal tracking may be defined with a three-dimensional position, and changes in that three-dimensional position may denote movement. In some examples, each joint of the virtual skeleton may also be defined with respect to rotational angle within the three-dimensional (3D) world space and with respect to a centerline of the virtual skeleton (e.g., 3D pose estimation).

For example, the system controller 116 may analyze the image information (e.g., via the image analysis module described with respect to FIG. 1) to identify the user 204 and build the user model 304, which may include identifying and analyzing the skeletal joints of the user 204 to determine movement, pose, position, etc. of the user 204. The system controller 116 may identify the patient 208 and build the patient model 308 similarly, such as by identifying and analyzing the skeletal joints of the patient 208 to determine movement, pose, position, etc. of the patient 208. The system controller 116 may further analyze the image information to build the probe model 306, such as by identifying the selected probe 106a, determining a temperature of the probe 106a (e.g., when the camera 130 includes thermal imaging), and tracking movement of the probe 106a.

As one example, the location and movement of the joints of the user 204 (as determined via the user model 304), the location and pose of the joints of the patient 208 (as determined via the patient model 308), and the location and movement of the selected probe 106a (as determined via the probe model 306) may be used to determine exam actions. For example, when the spatial exam model 300 shows the probe 106a being removed from the probe holder 212, the system controller 116 may activate the probe 106a. The system controller 116 may further begin a scanning sequence in response to the spatial exam model 300 showing the user 204 positioning the probe 106a on the patient 208 (e.g., via skeletal tracking of the user model 304 and the patient model 308 and position tracking of the probe model 306). In the above examples, activating the probe and beginning the scanning sequence are the exam actions. Additional exam actions and other actions taken by the system controller 116, such as pre-loading exam settings, will be described below with respect to FIG. 4.

As another example, based on the analyzed images, the system controller 116 may identify the type of probe 106 selected (e.g., probe 106a in the example of FIG. 3), which may be associated with a particular exam type (e.g., a curvilinear probe for an abdominal exam) or imaging mode (e.g., B-mode). The system controller 116 may update imaging settings of the ultrasound imaging system 100 based on the identified probe 106a and the associated exam type so that the ultrasound imaging system 100 is ready to perform the exam without any additional manual setup by the user 204.

Further, as described above, the ultrasound imaging system 100 may acquire medical imaging data, which may include two-dimensional and/or three-dimensional data that may be processed into one or more images for subsequent displaying and/or saving. However, saving all of the ultrasound images acquired during an ultrasound exam requires a large amount of storage memory. Additionally, such a relatively large number of saved images may pose a time burden on a clinician reviewing the images, which may unsuitably delay a diagnosis, for example. Therefore, the system controller 116 may selectively tag acquired ultrasound images for storage based on the position of the selected probe 106a on the patient 208 (e.g., as determined via the probe model 306 and the patient model 308, respectively, within the spatial exam model 300) and/or a motion/gesture of the user 204 (e.g., as determined via the user model 304). Then, only the tagged images may be saved, or the tagged images may be saved to a different memory than images that do not contain the "save" tag. For example, the tagged images may be saved to a PACS server memory (e.g., remote memory 124 of FIG. 1), and images that are not tagged may be saved to an internal memory of the medical imaging system (for example, memory 120 of FIG. 1). In a still further example, all of the images, regardless of tag status, may be saved to a first, temporary memory, such as a buffer or other temporary storage on the ultrasound system workstation, while only the tagged images may be saved to a second, remote memory, such as a PACS. Further, in some examples, the system controller 116 may analyze both the images received from camera 130 for building the spatial exam model 300 and ultrasound images acquired by the probe 106a to determine exam actions as well as which ultrasound images to tag for selective tagging, such as by tagging an entire volumetric data set and/or an entire cine loop of a beating heart.

Figure 4:
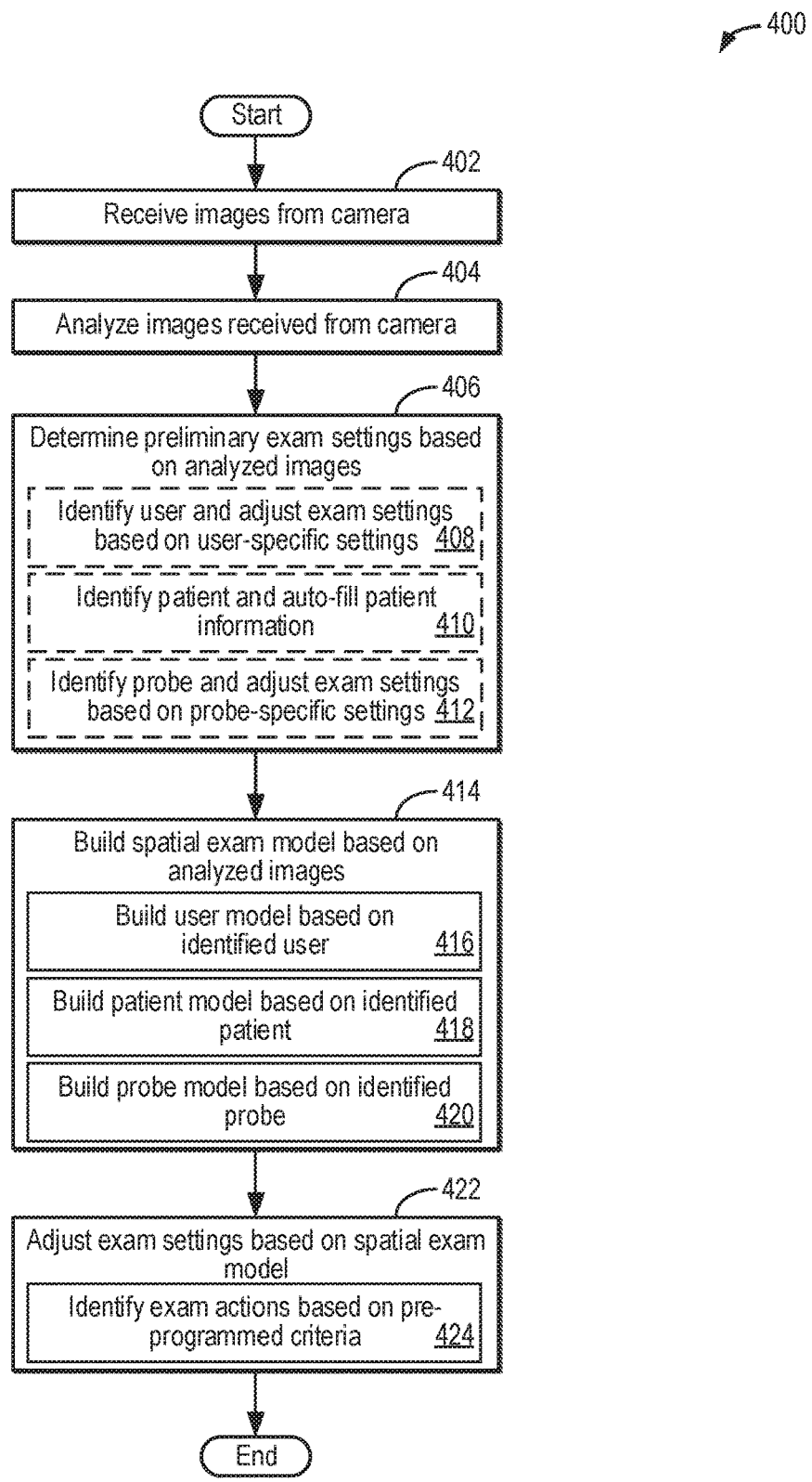
FIG. 4 is a flow chart illustrating a method for automated ultrasound exam setup and control via optical camera monitoring of an ultrasound exam environment.

Turning now to FIG. 4, a flow chart of an example method 400 for automating ultrasound exam setup and control via camera monitoring of the ultrasound exam is shown. The method 400 may be performed with an imaging system, such as the ultrasound imaging system 100 shown in FIGS. 1-3. More specifically, method 400 may be executed by a controller of the ultrasound imaging system (such as the system controller 116 shown in FIG. 1) according to instructions stored on a non-transitory memory of the system (e.g., memory 120 shown in FIG. 1) in combination with the various signals received at the controller from the system components, including a camera (e.g., camera 130 of FIGS. 1-3), and actuation signals sent from the system controller to actuators of the system (e.g., probe 106 of FIGS. 1-3). However, according to other embodiments, the method 400 may also be performed with other ultrasound imaging systems or with different medical imaging devices (e.g., MRI, PET, X-ray, or other similar systems).

Method 400 begins at 402 and includes receiving images from the camera. As described above with respect to FIGS. 1 and 2, the camera may include one or more cameras that capture images of a same or different wavelength range of electromagnetic radiation (such as visible or infrared light). For example, a plurality of cameras may be positioned at different locations within an exam room (e.g., exam room 202 shown in FIGS. 2 and 3) in order to provide images of different view angles to the controller. The different view angles may provide the controller with a more comprehensive view of the exam room, including the people and equipment positioned therein. Further, the camera(s) may capture a sequence of images at a pre-programmed frequency, such as a frequency in a range from 8-24 frames per second. Alternatively, the pre-programmed frequency may be greater than 24 frames per second or less than 8 frames per second. As one example, the pre-programmed frequency may be selected based on a processing speed of the controller so that each image may be fully analyzed before the controller receives a next image in the sequence. The controller may receive the images from the camera as they are acquired via wired or wireless communication methods, for example, Ethernet, USB, Bluetooth®, and WiFi.

At 404, the method includes analyzing the images received from the camera. As described above with respect to FIG. 1, the controller may include an image analysis module that analyzes the images received from the camera in real-time to identify one or more features within each of the received image. For example, the image analysis module may use one or any combination of an image library, a model, and an algorithm for recognizing one or more human subjects present in the exam room as well as ultrasound imaging system components, such as one or more probes. The one or more human subjects may include a patient and a user of the ultrasound imaging system (e.g., a sonographer). As one example, the controller may distinguish the patient from one or more additional human subjects present in the exam room based on the location of the human subject designated as the patient on an exam table. As another example, the controller may distinguish the user from one or more additional human subjects present in the exam room based on the location of the human subject designated as the user proximate to the ultrasound imaging system.

At 406, the method includes determining preliminary exam settings based on the analyzed images. This may include, for example, identifying the user and adjusting the exam settings based on user-specific settings, as indicated at 408. For example, once the controller determines which human subject is the user, the controller may further analyze the image, such as using a biometric algorithm that performs facial recognition, to positively identify the user. As an illustrative example, the biometric algorithm may compare a face of the user to identification photos of all possible users to positively identify the user. Further, the controller may store user-specific settings and information, including custom pre-sets associated with each possible user, in memory. Once the user is positively identified, the controller may access the stored user-specific settings and information associated with the identified user and adjust the exam settings accordingly, including updating imaging settings of the ultrasound imaging system. As one example, the user-specific settings and information may include personal information of the user (such as name, department, personal identification number, etc.). As another example, the user-specific settings and information may additionally or alternatively include speckle reduction filter presets, custom button configurations, custom workflow protocols, pre-defined application settings, etc. In this way, the controller may set up the ultrasound imaging system with the preferred settings of the identified user without the user manually inputting the settings or any personal information.

As still another example, positively identifying the user (e.g., via facial recognition) may be included as part of a two-step and/or ongoing authentication method for increased security and/or accuracy of record keeping. For example, identifying the user via the analyzed images may confirm that the identified user matches other credentials input into the ultrasound imaging system. For example, the user may log into the ultrasound imaging system workstation (e.g., via a user name and password), and the controller may confirm that the identified user matches the user credentials. This may ensure that the identified user does not perform an exam using another user's credentials. For example, a first sonographer may log in to the workstation with the intent of starting the exam but may be replaced by a second sonographer before the exam commences. Thus, the positive identification of the user may be leveraged to ensure the user authenticated by the workstation is the same one performing the exam. For example, the controller may lock the workstation or otherwise alert the second sonographer to enter their credentials.

As another example, determining the preliminary exam settings based on the analyzed images may additionally or alternatively include identifying the patient and automatically entering (e.g., auto-filling) patient information, as indicated at 410. For example, each patient may have an identification photo linked to their patient information, and a same or different biometric algorithm may compare a face of the patient to the identification photo of all patients stored in the system (or alternatively, all patients known to be scheduled for an ultrasound exam) to positively identify the patient (e.g., via facial recognition). The patient information may include, for example, name, birthday, vital statistics (e.g., weight, height, and blood pressure), pre-existing conditions, etc. As another example, if the patient has already had an ultrasound exam previous to the current exam, the controller may load the previous exam from an archive (such as accessed from remote memory 124 shown in FIG. 1). The preliminary exam settings may be further adjusted, such as by updating the ultrasound imaging system settings to those used for the previous exam.

As an example, the controller may determine a type of exam (such as prenatal, gynecological, etc.) based on the patient information and update the ultrasound imaging system settings according to a scan protocol associated with the type of exam and stored in memory, such as by beginning a specific scan workflow. As another example, the controller may additionally or alternatively determine an organ to be scanned during the ultrasound exam (such as ovaries or heart) based on the identified patient and adjust the ultrasound imaging system settings accordingly. As one illustrative example, the controller may activate an endocavity probe responsive to determining the gynecological exam type and may further adjust the ultrasound imaging system settings, such as ultrasound frequency, amplitude, and phase, to optimized pre-sets stored in memory for the gynecological exam. As another illustrative example, the controller may activate a probe optimized for obese patients responsive to the weight of the identified patient indicating that the patient is obese. In this way, the controller may set up the ultrasound imaging system with settings for imaging the identified patient without the user manually inputting the settings or any patient personal information.

Determining the preliminary exam settings based on the analyzed images may additionally or alternatively include identifying the probe and adjusting the exam settings based on probe-specific settings. For example, once the human subject identified as the user selects the probe, the controller may distinguish the selected probe from other probes based on its size, shape, or holder position on the ultrasound imaging system. As an example, the controller may utilize a probe identification algorithm stored therein to compare the selected probe to a plurality of possible probes to identify the type of probe selected. As another example, the controller may additionally or alternatively identify the probe based on a pre-programmed holder position of the probe stored in memory. As an illustrative example, a curvilinear probe may be programmed as occupying a first holder position, a linear probe may be programmed as occupying a second holder position, and a pulsed array probe may be programmed as occupying a third holder position. In response to the analyzed image showing the probe displaced from the first holder position, the controller may determine that the selected probe is the curvilinear probe and may adjust the exam settings to include settings for the curvilinear probe. For example, an ultrasound frequency may be set to a lower frequency when the selected probe is identified as a curvilinear probe and set to a higher frequency when the selected probe is identified as a linear probe. As another illustrative example, a biopsy needle guide may be attached to the selected probe when the ultrasound exam includes a biopsy examination. Responsive to the controller identifying the attached biopsy needle guide in the analyzed images from the camera, the controller may update the ultrasound imaging system settings to include specific presets for the biopsy examination that are stored in memory.

In still other examples, the controller may adjust a selection of exam pre-sets available to the user based on the identified probe. As still another example, probe-specific modes may be offered based on the identified probe (e.g., 3D/4D modes for volume probes). Additional actions, such as activating one or more auxiliary functions, may also be taken responsive to identifying the probe. The auxiliary functions may be probe-specific or may be performed regardless of the specific probe identified. As an illustrative example, responsive to identifying an endocavity probe as the selected probe, the controller may update the selection of available exam pre-sets to include gynecological and obstetrics presets, but not abdominal or heart imaging pre-sets. Further, the controller may activate a gel warmer and/or a DVD recording function. In this way, the controller may set up the ultrasound imaging system with settings for using the identified probe without the user manually inputting the settings or the probe type.

Further, in some examples, acquired ultrasound images may be analyzed to refine and/or confirm the probe model based on anatomical features captured in the ultrasound images. For example, if the controller predicts an endocavity probe based on the analyzed images, the identification may be validated when ultrasound images of the ovaries are then acquired. In some examples, the controller may identify the anatomical features in the captured images based on optical images received from the camera of the ultrasound display. Additionally or alternatively, the controller may directly analyze the acquired ultrasound images to determine the captured anatomical features (e.g., via the ultrasound image processing module 126 shown in FIG. 1).

At 414, the method includes building a spatial exam model based on the analyzed images. For example, the controller may not only identify the user, the patient, and/or the probe (e.g., at 406) based on the analyzed images and load corresponding settings (as applicable), but may also build a dynamic spatial model of the user, the patient, and the probe. Further, the controller may build the spatial exam model even if the user, the patient, and/or the probe is not positively identified (e.g., the unique identity of the user, the patient, and/or the probe type is not known).

Building the spatial exam model includes building a user model based on the identified user, as indicated at 416. For example, the controller may not only identify which of the human subjects is the user, but may track the user's position in space over time by continuously updating the user model as images are received from the camera (e.g., in real-time). Further, the controller may determine user gestures, for example, by tracking the user's position in space over time. As described above with respect to FIG. 3, the controller may map a first virtual skeleton to the user and perform skeletal tracking, wherein a plurality of joints of the user are identified and analyzed to determine movement, pose, position, etc. of the user.

Building the spatial exam model further includes building a patient model based on the identified patient, as indicated at 418. For example, the controller may not only identify which of the human subjects is the patient, but may track the patient's position in space over time by continuously updating the patient model in real-time. As described above with respect to FIG. 3, the controller may map a second virtual skeleton to the patient and perform skeletal tracking, wherein a plurality of joints of the patient are identified and analyzed to determine movement, pose, position, etc. of the patient. As another example, the patient model may include a body size parameter of the patient. For example, the controller may define the patient envelope (e.g., the surface area and volume of the patient), which in turn may be used to determine an approximate body mass index (BMI) of the patient.

Building the spatial exam model further includes building a probe model based on the identified probe, as indicated at 420. For example, the controller may not only identify which probe of the plurality of probes is selected, but may track its position in space over time to determine probe movement, such as by continuously updating the probe model as new images are received from the camera and analyzed.

At 422, the method includes adjusting the exam settings based on the spatial exam model. As one example, prior to scanning commencing, the controller may further adjust the ultrasound imaging system settings based on the approximate BMI of the patient determined via the patient model. For example, responsive to a high approximate BMI, the controller may adjust the settings to include pre-sets for obese patients. This may include, for example, adjusting a penetration depth of ultrasound waves produced by the selected ultrasound probe by adjusting the ultrasound frequency setting. As another example, the controller may adjust an amplitude and/or phase of the ultrasound waves produced by the selected ultrasound probe.

As another example, adjusting the exam settings based on the spatial exam model includes identifying exam actions based on pre-programmed criteria, as indicated at 424. For example, the spatial exam model may include spatial-temporal tracking of the probe model relative to the user model and the patient model. Each exam action may include pre-programmed criteria including, for example, a position/pose of the patient, a position/pose/gesture of the user, and a position/motion of the probe relative to the patient. The controller may identify exam actions based on the spatial exam model of the above mentioned parameters matching (e.g., fitting) the pre-programmed criteria. As a first illustrative example, criteria for an "activate probe" exam action may include the selected probe being removed from the probe holder by the user. Responsive to the spatial exam model showing removal of the selected probe from the probe holder by the user, the controller may activate (e.g., turn on) the selected probe. As a second illustrative example, criteria for a "deactivate probe" exam action may include the selected probe being replaced in the probe holder by the user. Responsive to the spatial exam model showing replacement of the selected probe in the probe holder, the controller may deactivate (e.g., turn off) the selected probe. As a third illustrative example, criteria for a "start scan" exam action may include the user placing the probe onto the patient. Responsive to the spatial exam model showing the user placing the selected probe onto the patient, the controller may actuate the selected probe to acquire ultrasound data.

As a fourth illustrative example, criteria for a "freeze image" exam action may include the user holding the selected probe still on the patient. Responsive to the spatial exam model indicating the user is holding the selected probe still on the patient, the controller may freeze the ultrasound image shown on a display screen. Additionally or alternatively, responsive to the user holding the selected probe still on the patient, the controller may acquire a plurality of ultrasound image frames, which may be combined in a reconstructed image for increased spatial resolution. In some such examples, the number of frames acquired may be adjusted based on the BMI of the patient (e.g., as determined via the patient model). Because spatial resolution of the ultrasound images (e.g., of the anatomical features captured in the ultrasound images) decreases with depth and deeper scanning depths may be used for obese patients, acquiring more frames for higher BMI patients (compared with lower BMI patients) may enable greater spatial resolution to be achieved.

As a fifth illustrative example, criteria for a "selective save" exam action may include a predetermined motion pattern of the probe and/or user. Responsive to the spatial exam model showing the predetermined motion pattern of the probe and/or the user, the controller may save (or tag for saving) the ultrasound data/images acquired during the predetermined motion pattern.

Method 400 may then end. In one example, the controller may continue to track the user, the patient, and the probe via the spatial exam model and continue adjusting the exam settings responsive to identified exam actions. As another example, the controller may repeat method 400 each time one or more human subjects enters the exam room so that each new exam can be identified and set up without manual input from the user, enabling greater ultrasound exam throughput and more dedicated patient focus.

Thus, the methods and systems described herein provide for automating set up of a medical imaging session (e.g., an ultrasound exam) based on images of the medical imaging session obtained from one or more cameras. The images may be analyzed via one or more computer vision models and/or algorithms to distinguish a user of a medical imaging system, a patient to be imaged, and an imaging probe (e.g., an ultrasound probe) from other persons and objects depicted in the images. In some examples, a unique identity of the user and/or the patient may be established, and settings of the medical imaging system may be adjusted according to known or anticipated setting preferences associated with the unique user and/or patient. In some examples, a body mass of the patient may be estimated, and the settings of the medical imaging system may be adjusted to include settings for imaging patients having the estimated body mass. In some examples, a probe type of the probe may be established, and the settings of the medical imaging system may be adjusted to include pre-determined settings associated with the probe type.

Further, the one or more computer vision models and/or algorithms may be used to build a spatial model of the user (e.g., via a user model), the patient (e.g., via a patient model), and the probe (e.g., via a probe model). The spatial model may enable spatial-temporal tracking of the user, the patient, and the probe within world space and relative to each other, enabling exam actions to be recognized for further automated control of the medical imaging session. As a result, the user may focus on performing the medical imaging and interacting with the patient instead of manually setting up the medical imaging system and triggering the exam actions. This may save time, lower an opportunity for user error, and increase a repeatability/robustness of the medical imaging session as well as increase patient satisfaction.

The technical effect of adjusting ultrasound exam settings based on a spatial exam model is to expedite the exam process and increase operator efficiency.

An example provides a method, comprising acquiring images of an ultrasound exam via a camera; analyzing the acquired images in real-time to build a spatial exam model; and adjusting settings of the ultrasound exam in real-time based on the spatial exam model. In examples, acquiring images of the ultrasound exam includes acquiring images of an ultrasound exam environment from at least one view angle via the camera. In examples, the ultrasound exam environment includes an ultrasound imaging system and a plurality of human subjects, and wherein analyzing the acquired images in real-time to build the spatial exam model includes identifying a patient from the plurality of human subjects and identifying a user of the ultrasound imaging system from the plurality of human subjects.

In one example, identifying the user of the ultrasound imaging system from the plurality of human subjects includes positively identifying the user via facial recognition, and wherein adjusting the settings of the ultrasound exam in real-time based on the spatial exam model includes adjusting settings of the ultrasound imaging system to preferred pre-sets associated with the user, the preferred pre-sets including pre-programmed settings for a frequency of ultrasound waves emitted by an ultrasound probe.

In another example, adjusting the settings of the ultrasound exam in real-time based on the spatial exam model includes adjusting settings of the ultrasound imaging system based on a body size of the identified patient, the settings including a frequency, amplitude, and phase of ultrasound waves emitted by an ultrasound probe. In another example, identifying the patient from the plurality of human subjects includes positively identifying the patient via facial recognition, and wherein adjusting the settings of the ultrasound exam in real-time based on the spatial exam model includes updating settings of the ultrasound imaging system based on previously used settings for the patient, the settings of the ultrasound exam including one or more of a frequency and amplitude of ultrasound waves emitted by an ultrasound probe.

In examples, the ultrasound imaging system includes one or more probes, and analyzing the acquired images in real-time to build the spatial exam model includes identifying a selected probe of the one or more probes. As an example, analyzing the acquired images in real-time to build the spatial exam model includes building a patient model from the identified patient, building a user model from the identified user of the ultrasound imaging machine, and building a probe model from the identified selected probe. In examples, the patient model and the user model each include skeletal tracking, and the spatial exam model includes tracking movement, pose, and position of the user relative to the patient to identify exam actions. In examples, the exam actions include activating the identified selected probe, beginning a scanning sequence using the identified selected probe, and stopping the scanning sequence.

Another example provides a method for performing an ultrasound exam, comprising: building a user model, a patient model, and a probe model based on images received from a camera and analyzed in real-time; tracking the user model, the patient model, and the probe model in real-time to identify an exam action; and adjusting operation of an ultrasound imaging system based on the identified exam action.

As an example, building the user model includes: identifying a user from a plurality of human subjects in the images received from the camera via one or more of an image recognition algorithm and a biometric algorithm; mapping a first virtual skeleton to the identified user; and determining one or more of position, pose, and movement of the identified user based on tracking of the first virtual skeleton. As an example, building the patient model includes: identifying a patient from the plurality of human subjects in the images received from the camera via one or more of the image recognition algorithm and the biometric algorithm; mapping a second virtual skeleton to the identified patient; and determining one or more of position, pose, and movement of the identified patient based on tracking of the second virtual skeleton. As an example, building the probe model includes identifying a selected probe from a plurality of possible probes, including identifying a probe type of the selected probe and a position of the selected probe, and wherein tracking the user model, the patient model, and the probe model in real-time to identify the exam action includes identifying a scan start as the exam action responsive to a position of the selected probe, the one or more of the position, pose, and movement of the identified user, and the one or more of the position, pose, and movement of the identified patient matching pre-determined criteria. In examples, adjusting operation of the ultrasound imaging system based on the identified exam action includes, responsive to identifying the scan start as the exam action, acquiring ultrasound images via the selected probe.

An example provides an ultrasound imaging system, comprising: an ultrasound probe; an optical camera; and a controller storing executable instructions in non-transitory memory that, when executed, cause the controller to: acquire ultrasound data via the ultrasound probe; acquire optical image data via the optical camera; analyze the acquired optical image data in real-time; and adjust settings for operating the ultrasound probe based on the analyzed optical image data in real-time.

In examples, to analyze the acquired optical image data in real-time, the controller includes further instructions stored in non-transitory memory that, when executed, cause the controller to: identify a user of the ultrasound imaging system in the acquired optical image data via one or more of an image recognition algorithm and a biometric algorithm; identify a patient in the acquired optical image data via one or more of the image recognition algorithm and the biometric algorithm; and identify a probe type of the ultrasound probe in the acquired optical image data via the image recognition algorithm.

As an example, the optical camera is configured to acquire optical image data at a predetermined frequency, and to adjust the settings for operating the ultrasound probe based on the analyzed optical image data in real-time, the controller includes further instructions stored in non-transitory memory that, when executed, cause the controller to: build a user model of the identified user; build a patient model of the identified patient; build a probe model of the identified probe type of the ultrasound probe; and track the user model, the patient model, and the probe model over time to determine exam actions via a spatial exam model.

As another example, the exam actions include freezing an ultrasound image, and to determine the exam actions, the controller includes further instructions stored in non-transitory memory that, when executed, cause the controller to: determine motion of the user via the user model; determine a location of the probe relative to the patient and the user via the spatial exam model; and freeze the ultrasound image responsive to the determined motion of the user indicating the user is still and the determined location of the probe relative to the patient and the user indicating the user is holding the probe on the patient. In examples, the user model includes skeletal tracking of the user to determine the motion of the user.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. An ultrasound imaging system, comprising:
an ultrasound probe;
an optical camera; and
a controller storing executable instructions in non-transitory memory that, when executed, cause the controller to:
acquire ultrasound data via the ultrasound probe;
acquire optical image data via the optical camera;
analyze the acquired optical image data in real-time; and
adjust settings for operating the ultrasound probe based on the analyzed optical image data in real-time;
wherein to analyze the acquired optical image data in real-time, the controller includes further instructions stored in non-transitory memory that, when executed, cause the controller to:
identify a user of the ultrasound imaging system in the acquired optical image data via one or more of an image recognition algorithm and a biometric algorithm;
identify a patient in the acquired optical image data via one or more of the image recognition algorithm and the biometric algorithm; and
identify a probe type of the ultrasound probe in the acquired optical image data via the image recognition algorithm;
wherein the optical camera is configured to acquire optical image data at a predetermined frequency, and to adjust the settings for operating the ultrasound probe based on the analyzed optical image data in real-time, the controller includes further instructions stored in non-transitory memory that, when executed, cause the controller to:
build a user model of the identified user;
build a patient model of the identified patient;
build a probe model of the identified probe type of the ultrasound probe; and
track the user model, the patient model, and the probe model over time to determine exam actions via a spatial exam model, wherein the exam actions include freezing an ultrasound image, and to determine the exam actions, the controller includes further instructions stored in non-transitory memory that, when executed, cause the controller to:
determine motion of the user via the user model;
determine a location of the probe relative to the patient and the user via the spatial exam model; and
freeze the ultrasound image responsive to the determined motion of the user indicating the user is still and the determined location of the probe relative to the patient and the user indicating the user is holding the probe on the patient.

2. The system of claim 1, wherein the user model includes skeletal tracking of the user to determine the motion of the user.

3. An ultrasound imaging system, comprising:
an ultrasound probe;
an optical camera; and
a controller storing executable instructions in non-transitory memory that, when executed, cause the controller to:
acquire ultrasound data via the ultrasound probe;
acquire optical image data via the optical camera;
analyze the acquired optical image data in real-time to build a spatial exam model; and
adjust settings for operating the ultrasound probe in real-time based on the spatial exam model, wherein to analyze the acquired optical image data in real-time, the controller including further instructions stored in non-transitory memory that, when executed, cause the controller to:
identify a user of the ultrasound imaging system in the acquired optical image data via one or more of an image recognition algorithm and a biometric algorithm;
identify a patient in the acquired optical image data via one or more of the image recognition algorithm and the biometric algorithm; and identify a probe type of the ultrasound probe in the acquired optical image data via the image recognition algorithm, wherein the optical camera is configured to acquire optical image data at a predetermined frequency, and to adjust the settings for operating the ultrasound probe based on the analyzed optical image data in real-time, the controller including further instructions stored in non-transitory memory that, when executed, cause the controller to:

build a user model of the identified user;

build a patient model of the identified patient;

build a probe model of the identified probe type of the ultrasound probe; and track the user model, the patient model, and the probe model over time to determine exam actions via a spatial exam model, wherein the user model includes skeletal tracking of the user.

4. The system of claim 3, wherein the optical camera is mounted on a display device.

5. The system of claim 3, wherein the optical camera is wall-mounted in a same room as the ultrasound imaging system.

6. The system of claim 3, wherein the optical camera includes one or more visible light cameras, one or more infrared (IR) cameras, or a combination of optical and IR cameras positioned in one or more locations.

7. The system of claim 3, wherein the optical camera includes a digital camera configured to acquire a series of images at a programmable frequency.

8. The system of claim 3, wherein the optical camera is configured to output acquired images to the controller in real-time so that they may be processed in real-time.

9. The system of claim 3, wherein the optical camera is calibrated with respect to a world coordinate system.

10. The system of claim 3, wherein the controller is configured to adjust the settings automatically.

11. The system of claim 1, wherein the optical camera is mounted on a display device.

12. The system of claim 1, wherein the optical camera is wall-mounted in a same room as the ultrasound imaging system.

13. The system of claim 1, wherein the optical camera includes one or more visible light cameras, one or more infrared (IR) cameras, or a combination of optical and IR cameras positioned in one or more locations.

14. The system of claim 1, wherein the optical camera includes a digital camera configured to acquire a series of images at a programmable frequency.

15. The system of claim 1, wherein the optical camera is configured to output acquired images to the controller in real-time so that they may be processed in real-time.

16. The system of claim 1, wherein the optical camera is calibrated with respect to a world coordinate system.

17. The system of claim 1, wherein the controller is configured to adjust the settings automatically.

* * * * *